United States Patent [19]

Siegmund et al.

[11] Patent Number: 4,580,551
[45] Date of Patent: Apr. 8, 1986

[54] FLEXIBLE PLASTIC TUBE FOR ENDOSCOPES AND THE LIKE

[75] Inventors: Walter P. Siegmund, Pomfret Center, Conn.; George J. Carpenter, Southbridge, Mass.

[73] Assignee: Warner-Lambert Technologies, Inc., Morris Plains, N.J.

[21] Appl. No.: 667,834

[22] Filed: Nov. 2, 1984

[51] Int. Cl.[4] .............................................. A61B 1/06
[52] U.S. Cl. ....................................................... 128/4
[58] Field of Search .................... 128/4, 6; 350/96.26; 604/280, 281, 282; 138/118

[56] References Cited

U.S. PATENT DOCUMENTS

| | | | |
|---|---|---|---|
| 3,739,770 | 6/1973 | Mori | 128/6 |
| 3,946,727 | 3/1976 | Okada et al. | 128/4 |
| 4,290,421 | 9/1981 | Siegmund | 128/6 |
| 4,465,482 | 8/1984 | Tittel | 604/280 |

Primary Examiner—William H. Grieb
Attorney, Agent, or Firm—R. S. Strickler

[57] ABSTRACT

An elongated, flexible plastic tube with internal web and bore structure comprising a continuous sequence of connected vertebra-like elements useful in endoscopes and the like.

7 Claims, 4 Drawing Figures

FLEXIBLE PLASTIC TUBE FOR ENDOSCOPES AND THE LIKE

BACKGROUND OF THE INVENTION

The present invention relates to flexible tubes and relates in particular to flexible plastic tubes useful in endoscopes or in similar diagnostic medical, veterinary or industrial appliances.

The prior art is replete with such flexible tubes, representative examples of which are shown and described in U.S. Pat. Nos. 3,739,770 and 3,946,727 issued June 19, 1973, and Mar. 30, 1976, respectively, and both assigned on the face of each patent to Olympus Optical Co., Ltd., Tokyo, Japan.

The '770 patent shows a pair of helically wound metal strips 41 and 42 wound in opposite hands.

The '727 reference shows a single helical winding metal 11 covered by resin sheath 13.

Other structures comprise a string of metal or plastic rings connected together in one fashion or another so that the rings pivot or telescope partially into one another to encourage flexibility.

It is a principal object of the present invention to provide a novel plastic flexible tube structure that requires no helical winding or connecting of individual piece-parts.

It is a further object of the invention to provide a flexible tube comprising an endless series of connected vertebra-like elements.

A still further feature of the invention is the provision of a low-cost flexible tube for medical, veterinary and industrial endoscopes providing internal access for tube manipulation wires, and channels for conventional accessories such as vacuum, irrigation, forceps and the like.

SUMMARY OF THE INVENTION

A flexible plastic tube embracing certain principles of the invention may comprise an elongated plastic extrusion or injection molding defining a tube having a generally circular wall, said tube having an internal, elongated web structure incorporating a central lumen or bore all coextensive with said tube, a plurality of secondary bores formed in the tube wall and a plurality of cut-outs formed in said wall along the length of the tube effective to make the tube more flexible while preserving the integrity of the central bore or bores.

Other features and advantages of the invention will become more apparent from an examination of the succeeding specification when read in conjunction with the appended drawings, in which;

DESCRIPTION OF PREFERRED EMBODIMENT

Figure 1:
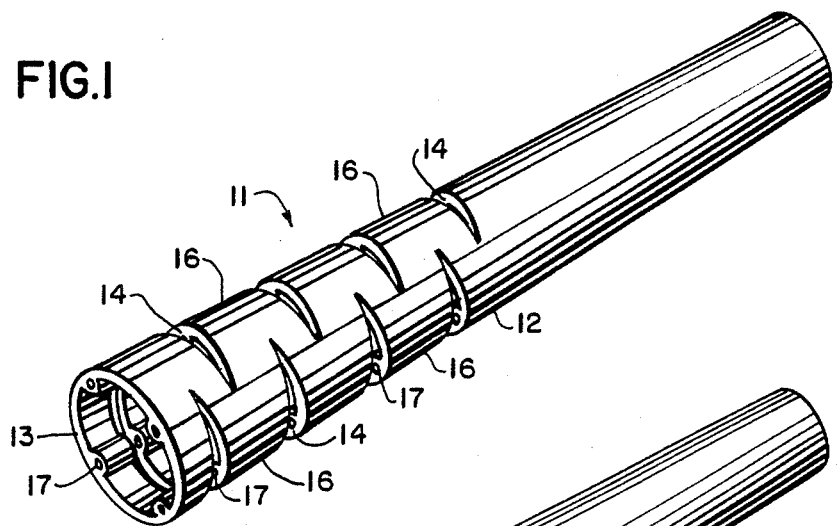
FIG. 1 is a perspective view of one embodiment of the flexible tube of the present invention.

Referring in detail to the drawings, the reference numeral 11 indicates a basic embodiment of the invention in which an extruded, drawn or injection molded, flexible plastic tube 12 having a wall 13 is formed with a plurality of cut-outs 14-14 which intersect the wall to define a continuous series of connected vertebra-like elements 16.

The wall is also formed with a number of bores 17-17 which, in some cases, are intercepted by the cut-outs 14.

The bores 17-17 provide a channel for wires used to manipulate the distal end or head of an endoscope in well-known fashion.

Figure 2:
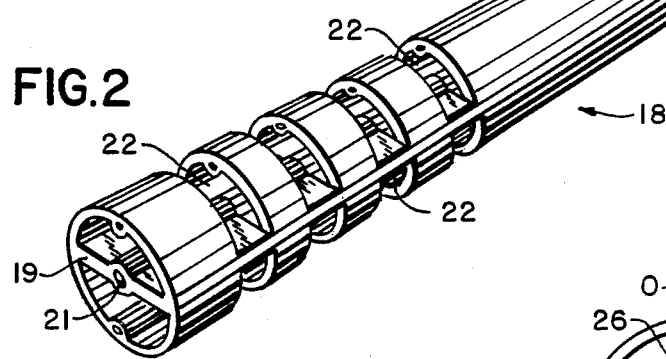
FIG. 2 is a similar view showing an alternative embodiment.

In FIG. 2, the tube, indicated generally by the reference numeral 18, is formed with an internal web 19 supporting a central lumen or bore 21. Here the notches or cut-outs 22 are disposed in opposed pairs and do not intersect or disturb the continuity of the web 19 or the bore 21.

Figure 3:
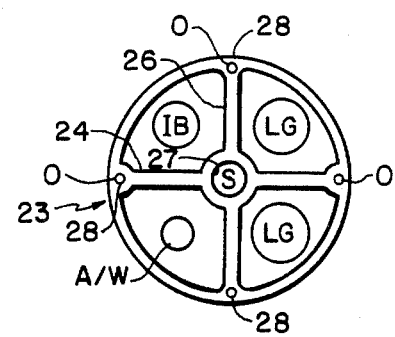
FIG. 3 is a sectional view of a tube showing a still further embodiment.

In the FIG. 3 embodiment, the interior of the tube, indicated generally at 23, includes cross webs 24 and 26 supporting central bore 27.

Four secondary bores 28-28 are provided to receive wires making it possible to manipulate a distal end universally.

In this embodiment, cut-outs are disposed in opposed pairs, but their position is rotated 90° in alternating pairs to avoid undue loss of body or strength in the overall tube.

Figure 4:
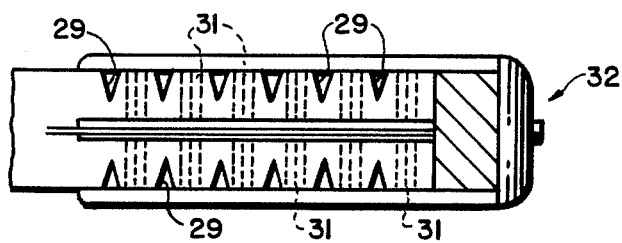
FIG. 4 shows a segment of a tube fitted with a head at the distal end and a membranous cover or sleeve.

This alternating position of opposed pairs of cut-outs is shown most clearly at 29 and 31 in FIG. 4.

FIG. 4 also shows a membranous skin or sleeve (greatly enlarged) of elastomeric material enclosing the tube 23 to seal the tube.

The reference numeral 32 denotes a distal end of a scope.

The following legend or schedule details the meaning of the various indicia in FIG. 3:

IB=image fiber optics bundle
LG=light guide bundle
S=suction or vacuum
O=wires for manipulation
A/W=air or water It is anticipated that a wide variety of embodiments may be devised in the disclosed invention without departing from the spirit or scope thereof. For example, the cross-sectional configuration of the tube and the pattern of notches can be designed in a variety of ways as various scope requirements dicate.

What is claimed is:

1. An elongated, flexible plastic structure defining a continuous sequence of connected vertebra-like elements useful in endoscopes and the like comprising:
an elongated plastic extrusion or injection molding defining a tube having a generally circular wall, said tube having an internal, elongated web structure incorporating a central lumen or bore all coextensive with said tube, a plurality of secondary bores formed in the tube wall and a plurality of cut-outs formed in said wall along the length of the tube effective to make the tube more flexible while preserving the integrity of the central bore.

2. The structure of claim 1 in which the cut-outs intersect the secondary bores.

3. The structure of claim 2 in which the cut-outs are V-shaped in cross-sectional configuration.

4. The structure of claim 2 in which the cut-outs are arranged according to a uniform pattern in opposed pairs.

5. The structure of claim 1 in which the cut-outs are sealed by a thin-walled elastomeric, membranous sheet.

6. The structure of claim 5 in which the sheet defines a sleeve overlaying the exterior of the tube.

7. The structure of claim 1 in which the internal web structure defines two intersecting webs dividing the internal cross-sectional area of the tube into four independent sectors or quadrants each coextensive with the tube.

* * * * *